United States Patent [19]

Fujisawa

[11] Patent Number: 5,258,065
[45] Date of Patent: Nov. 2, 1993

[54] INK COMPOSITION FOR INDICATING THE PROGRESS OF STERILIZATION WITH ETHYLENE OXIDE

[75] Inventor: Toshiki Fujisawa, Hirakata, Japan

[73] Assignee: Sakura Color Products Corporation, Osaka, Japan

[21] Appl. No.: 903,444

[22] Filed: Jun. 24, 1992

[30] Foreign Application Priority Data

Jun. 24, 1991 [JP] Japan ................... 3-151914

[51] Int. Cl.$^5$ .................... C09D 11/02; G01N 31/22
[52] U.S. Cl. ................... 106/22 B; 106/22 K; 436/1
[58] Field of Search .............. 106/23 B, 22 B, 22 K; 436/1

[56] References Cited

U.S. PATENT DOCUMENTS 4,015,937 4/1977 Miyamoto et al. ............... 436/1
4,171,301 10/1979 Mory .......................... 106/496

FOREIGN PATENT DOCUMENTS 60-15330 4/1985 Japan .
60-243173 12/1985 Japan .
1-19706 4/1989 Japan .

Primary Examiner—Helene Klemanski
Attorney, Agent, or Firm—Larson and Taylor

[57] ABSTRACT

An ink composition for indicating the progress of sterilization with EO is provided which comprises;
(1) at least one disperse dye of the general formula $$A-N=N-B$$

wherein A is the residue of a heterocyclic compound containing nitrogen atom which is not substituted with alkyl group and selected from the group consisting of the pyridine, quinoline, isoquinoline, triazole, tetrazole, indazole, thiazole, benzothiazole and thiadiazole rings, which residue may optionally have one or more undissociated substituents, and B is a coupling component,
(2) at least one binder component selected from the group consisting of polyacrylic acid, polymethacrylic acid and acrylic acid-methacrylic acid copolymers,
(3) at least one ultrafine filler selected from the group consisting of ultrafine particles of silica, aluminum oxide and titanium oxide, and
(4) at least one polar solvent.

10 Claims, 1 Drawing Sheet

INK COMPOSITION FOR INDICATING THE PROGRESS OF STERILIZATION WITH ETHYLENE OXIDE

FIELD OF THE INVENTION

The present invention relates to an ink composition for indicating the progress of sterilization with ethylene oxide. The ink composition is excellent in printability, develops a distinct color under optimum sterilization conditions, and shows highly improved characteristics as compared with the prior art ink compositions.

In the present specification, "%" and "part(s)" mean "% by weight" and "part(s) by weight", respectively.

PRIOR ART

In recent years it has become a common practice to sterilize medical appliances and supplies, for instance, by placing the objects to be sterilized in an airtight container or vessel and introducing ethylene oxide gas (EO) thereinto. Usually, an ink capable of changing its color upon attainment of appropriate sterilization conditions is printed or provided, as an indicator or label, on the objects to be sterilized and the completion of sterilization is judged by the color change of the indicator inks.

Various EO sterilization indicator ink are known. For instance, Japanese Kokai Tokkyo Koho No. 60-243173 discloses an ink composition comprising (a) a dye having a specific structure, (b) at least one member of the group consisting of polyacrylic acid, polymethacrylic acid and acrylic acid-methacrylic acid copolymers and (c) a polar solvent. Japanese Kokoku Tokkyo Koho No. 01-19706 discloses an ink composition comprising, as essential components, a disperse dye represented by the general formula A—N=N—B (wherein A is the residue of a heterocyclic compound containing one or more alkyl-free nitrogen atoms as selected from the group consisting of the pyridine, quinoline, isoquinoline, triazole, tetrazole, indazole, thiazole, benzothiazole and thiadiazole rings, which residue may optionally have one or more undissociated substituents, and B is a conventional coupling component), a water-soluble high molecular compound, an organic acid and water. While these ink compositions have better properties as compared with the ink compositions of the same kind heretofore known, they tend to foam and are therefore inferior in printability. Further, the color development under optimum sterilization conditions is not invariably distinct and, in particular, the difference in color change between the optimum humidity conditions for sterilization (30 to 80% humidity) and the inadequate humidity conditions (less than 30% humidity) is not clearly indicated.

Accordingly, EO sterilization indicator ink compositions having excellent printability and capable of distinct color development under optimum sterilization conditions are desired.

SUMMARY OF THE INVENTION

In view of the above-mentioned state of the art, the present inventors have made extensive investigations and found that the performance of the ink composition as an EO sterilization indicator can be markedly improved by incorporation of an ultrafine filler.

The invention provides an ink composition for indicating the progress of sterilization with EO which composition is excellent in printability and capable of changing its color distinctly under optimum sterilization conditions.

The ink composition of the invention comprises;

(1) at least one disperse dye of the general formula

wherein A is the residue of a heterocyclic compound containing nitrogen atom which is not substituted with alkyl group and selected from the group consisting of the pyridine, quinoline, isoquinoline, triazole, tetrazole, indazole, thiazole, benzothiazole and thiadiazole rings, which residue may optionally have one or more undissociated substituents, and B is a coupling component, (2) at least one binder component selected from the group consisting of polyacrylic acid, polymethacrylic acid and acrylic acid-methacrylic acid copolymers, (3) at least one ultrafine filler selected from the group consisting of ultrafine particles of silica, aluminum oxide and titanium oxide, and (4) at least one polar solvent.

The present invention further provides a method of indicating the state of ethylene oxide sterilization which method comprises using the ink composition specified above.

DETAILED DESCRIPTION OF THE INVENTION

The disperse dye to be used in the present invention is represented by the general formula

wherein A is the residue of a heterocyclic compound containing one or more nitrogen atoms which are not substituted with alkyl group : the residue is selected from the group consisting of the pyridine, quinoline, isoquinoline, triazole, tetrazole, indazole, thiazole, benzothiazole and thiadiazole rings, which residue may optionally have one or more undissociated substituents, and B is a conventional coupling component. These dyes can be used singly or in combination of two or more kinds. A very wide variety of dyes are represented by the above general formula and therefore a dye or dyes showing a distinct color change after EO gas treatment can suitably be selected depending on sterilization and other conditions.

Referring to the above general formula, the heterocyclic compound residue represented by A includes, for example, the following groups.

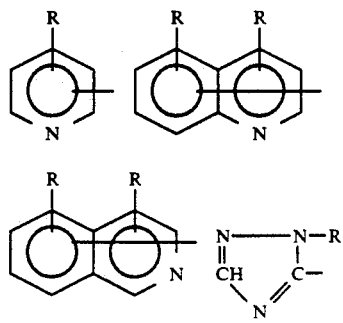

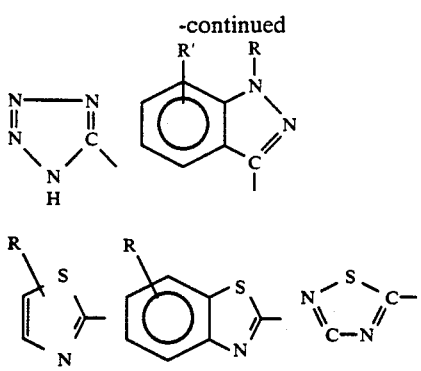

As the R and R' groups in the foregoing examples of the heterocyclic compound residue A, there may be mentioned, for example, methyl, ethyl, ethoxy, halogen atom, cyano, nitro, hydroxyl, amino, dimethylamino, diethylamino, diethanolamino, carboxyl, phenyl, phenoxy, benzyl, sulfonic acid, anilino and acetamido.

The coupling component B in the above general formula may be selected from a wide variety of coupling components generally used in synthesizing coloring matters. More specifically, the following example may be given.

Aromatic amines—aminobenzene, dimethylaminobenzene, diethanolaminobenzene, 1-amino-2-methylbenzene, 1-amino-3-methylbenzene, 1-amino-2,5-dimethylbenzene, 1-amino-2-methoxy-5-methylbenzene,1,3-diaminobenzene,1,3-diamino-4-chlorobenzene, 1,3-diamino-4-nitrobenzene, 2,4-diaminobenzenesulfonic acid, 4,6-diamino-1,3- benzenedisulfonic acid, etc.

Phenols—phenol, p-cresol, resorcinol, 1,3,5-benzenetriol, salicylic acid, 3-methylsalicylic acid, etc.

Naphthols—α-naphthol, β-naphthol, 1,5-naphthalenediol, 1-hydroxy-3-naphthalenesulfonic acid, 1-hydroxy-4-naphthalenesulfonic acid, 1-hydroxy-5-naphthalenesulfonic acid, 1-hydroxy-3,6-naphthalenedisulfonic acid, 2-hydroxy-6,8-naphthalenedisulfonic acid, 1,8-dihydroxy-4-naphthalenesulfonic acid, 1,8-dihydroxy-3,6-naphthalenedisulfonic acid, etc.

Aminophenols—1-amino-2-hydroxybenzene, 1-amino-2-hydroxy-5-methylbenzene, 1-amino-2,5-dihydroxybenzene, etc.

Aminonaphthols—1-amino-3-naphthalenesulfonic acid, 1-amino-2-naphthalenesulfonic acid, 1-anilide-7-naphthalenesulfonic acid, 2-amino-3,6-naphthalenedisulfonic acid, 2-amino-3-naphthalenecarboxylic acid, 1-hydroxy-6-amino-3-naphthalenesulfonic acid, 1-amino-8-hydroxy-4-naphthalenesulfonic acid, 1-amino-8-hydroxy-2,4-naphthalenedisulfonic acid, 1-amino-5-hydroxy-7-naphthalenesulfonic acid, 1-amino-2-ethoxy-6-naphthalenesulfonic acid, 3-hydroxy-2-naphthanilide, etc.

Others—5-oxo-3-methyl-1-phenyl-2-pyrazoline, 5-oxophenyl-2-pyrazoline-3-carboxylicacid, 1-(4-sulfophenyl)-5-oxo-1-methyl-2-pyrazoline, 5-imino-3-methyl-1-phenyl-2-pyrazoline, and other reactive methylene-containing, enolizable compounds.

As preferred examples of the disperse dye of the above general formula, there may be mentioned C.I. disperse Red 58 (A: benzothiazole; B: diethanolaminobenzene), 88, 111 or 206, C.I. Disperse Violet 43, C.I. Disperse Blue 102 and the like.

The ink composition of the present invention may contain a small amount of a known water-soluble dye for toning, when required.

In the ink composition of the invention, at least one polymer selected from the group consisting of polyacrylic acid, polymethacrylic acid and acrylic acid-methacrylic acid copolymers is used as the binder component. The polymers are required only to be soluble in the liquid component, namely polar solvent, capable of giving weakly acidic aqueous solutions or dispersions, and hygroscopic in the dry paint film form, without any other particular limitations. These binder components are commercially available, generally in the form of aqueous dispersions, and these dispersions may be used as such. From the viewpoint of printability of ink, polyacrylic acid and acrylic acid-methacrylic acid copolymers are preferred as the binder component. Such polymers preferably have a molecular weight of about 4,000 to about 8,000.

It is very important that at least one ultrafine filler selected from the group of ultrafine powders of silica, aluminum oxide and titanium oxide should be used in the ink composition of the present invention. Such a filler has a large surface area and therefore increases the hygroscopicity of the film formed upon application of the EO sterilization indicator ink composition on a surface. As a result, the color change under optimum humidity conditions for sterilization (30 to 80% humidity) is enhanced. Thus the difference in color development between the optimum humidity conditions and the inadequate humidity conditions for sterilization temperature becomes distinct, so that the state of optimum sterilization (in particular humidity condition) can be indicated more correctly. In the ink composition, secondary particles of the ultrafine filler as resulting from aggregation or agglomeration further bind to one another to form a kind of network structure, producing additional effects, for example preventing the composition from blocking during storage, preventing the cobwebbing during application, and providing the ink composition with adequate thixotropic properties to,thereby prevent sagging following application. As a result, the printability is stable and the uniformity of printed surface is ensured. The ultrafine filler preferably has a mean primary particle size of about 5 to about 100 nm and a specific surface area of about 10 to about 1,000 $m^2/g$ as determined by the BET method. Ultrafine particles of aluminum oxide is more preferred as the ultrafine filler.

The polar solvent to be used in the ink composition of the present invention includes, for example, water, aliphatic alcohols, ketones, glycol ethers, esters, and the like. These solvents may be used either singly or in a mixture of two or more of them. Examples of the polar solvent other than water are as follows.

Aliphatic alcohols—Ethanol, n-propyl alcohol, isopropyl alcohol, butanol, pentanol, etc.

Ketones—Methyl ethyl ketone, methyl n-propyl ketone, methyl isobutyl ketone, etc.

Glycol ethers—Ethylene glycol monoethyl ether, ethylene glycol monobutyl ether, diethylene glycol monoethyl ether, diethylene glycol monopropyl ether, etc.

Esters—Ethyl acetate, n-butyl acetate, ethyl propinoate, methyl butyrate, etc.

Among the polar solvents mentioned above, water, aliphatic alcohols and glycol ethers are preferred.

The ink composition of the present invention which is intended to provide an EO sterilization indicator comprises, as essential components thereof, (1) the disperse dye of the general formula A—N=N—B in an amount of 0.05 to 3% (preferably 0.1 to 2%), (2) the binder component in an amount of 0.5 to 50% (preferably 2 to 30%), (3) the ultrafine filler in an amount of 0.05 to 10% (preferably 0.3 to 5%) and (4) the polar solvent in an amount of 30 to 95% (preferably 40 to 92%), based on the total weight of the ink.

When the amount of the disperse dye of the general formula A—N=N—B is below 0.05%, the color development becomes insufficient, hence the color difference (before and after color development) will be small. When the amount exceeds 3%, the rate of color change becomes slow.

When the content of the binder component is less than 0.5%, the humidity detecting effect is low and the color development is poor. Conversely, when the binder component is present in an amount exceeding 50%, the ink will be highly viscous and low in the printability and the formed ink film will be brittle.

When the content of the ultrafine filler is less than 0.05%, the humidity detecting effect cannot be improved to a satisfactory extent and the improvement in printability is not sufficient. On the other hand, use of ultrafine filler in an amount exceeding 10% results in an excessively high viscosity, hence in poor printability.

When the polar solvent is used in an amount smaller than 30%, an excessively high viscosity results, leading to inferior printability. In an amount exceeding 95%, the ink film formation is difficult. When water is used as the polar solvent, the amount of water contained in the aqueous resin dispersion, which is the binder component source, is considered as a part of the solvent component.

Other materials may be incorporated in the ink composition of the present invention for improving performance.

For instance, for improving the film-forming properties, any of those resins which are used as binder components in known oil-based inks may be incorporated as an auxiliary component. Examples of such auxiliary component resin are carboxyl- or phenolic hydroxyl group-containing resins (e.g. rosin, maleic acid resins, alkylphenol resins, etc.) and cellulosic resins. These resins are used in an amount up to 50% by weight based on the total weight of ink. When these resins are used in an amount exceeding 50% of the ink weight, the viscosity of the ink is too high, whereby the printability is deteriorated.

In cases where the binder component cannot be incorporated in the ink composition in a sufficient amount for some reasons and, accordingly, the humidity detecting effect cannot be produced to a significant extent, at least one organic acid can be incorporated in an amount up to 10% of the total ink weight. Examples of organic acid additionally used are as follows.

Aliphatic dicarboxylic acids—Oxalic acid, malonic acid, maleic acid, etc.
Sulfonic acids—Butanesulfonic acid, butanedisulfonic acid, benzenesulfonic acid, etc.
Aromatic acids—Phenol, benzoic acid, phthalic acid, salicylic acid, Sulfosalicylic acid, etc.

Particularly, when the organic acid is a polybasic acid, at least one of the acidic radicals may be a free acidic radical while the other acidic radical or radicals may be in a salt form. The use of such a polybasic acid, for example, sodium sulfosalicylate or zinc salicylate, favorably results in improved stability of ink films.

Furthermore, surfactants, preservatives, rust preventives, perfumes and like additives that are conventionally used in known water-based ink compositions may be incorporated in the ink composition of the present invention, as required.

The ink composition of the present invention can be produced by any method provided that all the constituents used can give a uniform dispersion. For example, an ink composition according to the present invention can be prepared by admixing the disperse dye, binder resin and polar solvent with stirring and heating at about 50° C. to give a uniform dispersion, then adding the ultrafine filler and further stirring the mixture with heating at about 50° C. In cases where an auxiliary component resin and/or organic acid is used, such optional component is preferably added prior to the addition of the ultrafine filler.

In accordance with the present invention, an EO sterilization indicator ink composition can be obtained which is excellent in printability and shows a distinct color change under optimum sterilization conditions for EO sterilization treatment.

EXAMPLES

The following examples and comparative examples are given to illustrate the features of the present invention.

The materials used in the examples and comparative examples are as specified below.

A. Disperse dye
    A-1—C.I. Disperse Red 58 ("Miketon Fast Pink FR"; Mitsui Toatsu Chemicals, Inc.) (A: benzothiazole; B: diethanolaminobenzene)
    A-2—C.I. Disperse Violet 43 ("Miketon Discharge Pink 3B"; Mitsui Toatsu Chemicals, Inc.)
    A-3—C.I. Disperse Red 111 ("Miketon Polyester Red BSF"; Mitsui Toatsu Chemicals, Inc.)

B. Binder component
    B-1—50% Aqueous solution of acrylic acid-methacrylic acid copolymer ("Jurimer AC-20L"; Nihon Junyaku Co., Ltd.)
    B-2—Polyacrylic acid ("Hiviswako 103"; Wako Pure Chemical Industries, Ltd.)
    B-3—Polyacrylic acid ("Jurimer AC-10LP"; Nihon Junyaku Co., Ltd.)
    B-4—Polymethacrylic acid ("Jurimer AC-30H"; Nihon Junyaku Co., Ltd.)
    B-5—50% Aqueous solution of acrylic acid-methacrylic acid copolymer ("Jurimer AC-10L"; Nihon Junyaku Co., Ltd.)
    B-6—Polyacrylic acid ("Jurimer AC-20LP"; Nihon Junyaku Co., Ltd.)

C. Ultrafine filler
    C-1—Ultrafine aluminum oxide ("Aluminium Oxide C"; Degussa AG; mean primary particle size=about 20 nm, specific surface area determined by the BET method= $100 \pm 15$ m$^2$/g)
    C-2—Ultrafine silica ("Aerosil 200"; Degussa AG; mean primary particle—size about 12 nm, specific surface area determined by the BET method= $200 \pm 25$ m$^2$/g)
    C-3—Ultrafine titanium oxide ("Titanium Oxide P25"; Degussa AG; mean primary particle size=about 30 nm, specific surface area determined by the BET method= $50 \pm 15$ m$^2$/g)
    C-4—Mixture of ultrafine silica and ultrafine aluminum oxide ("Aerosil MOX80"; Degussa AG; mean primary particle=size about 30 nm, specific surface area determined by the BET method = $80\pm25$ m$^2$/g)

C-5—Ultrafine silica ("Tokusil UR"; Tokuyama Soda Co., Ltd.; mean primary particle size = about 16 nm, specific surface area determined by the BET method = $200\pm25$ m$^2$/g)

C-6—Ultrafine silica ("Syloid 65"; Fuji-Davison Chemical, Ltd.; mean primary particle size = about 10 nm, specific surface area determined by the BET method = 700 m$^2$/g)

C-7.—Mixture of ultrafine silica and ultrafine aluminum oxide ("Aerosil MOX170"; Degussa AG: mean primary particle size about 15 nm, specific surface area determined by the BET method = $170\pm30$ m$^2$/g)

D. Polar solvent
  D-1—Ethylene glycol monoethyl ether
  D-2—Isopropyl alcohol
  D-3—Propylene glycol monomethyl ether
  D-4—Deionized water
  D-5—Ethyl alcohol E. Basic dye
  E-1—C.I. Basic Yellow 24 ("Kayacryl Brilliant Yellow 5GL")

F. Auxiliary resin component
  F-1—Maleic acid resin ("Malkyd No. 33"; Arakawa Chemical Industries, Ltd.)
  F-2—Hydroxypropylcellulose ("HPC-SL"; Nippon Soda Co., Ltd.)
  F-3—Rosin ("KR-610"; Arakawa Chemical Industries, Ltd.)
  F-4—Alkylphenol resin ("Tamanol 100S"; Arakawa Chemical Industries, Ltd.)
  F-5—Hydroxyethylcellulose ("EP500", Daicel Chemical Industries, Ltd.)

G. Organic acid
  G-1—Sodium sulfosalicylate dihydrate
  G-2—2-Hydroxy-3-naphthoic acid
  G-3—Zinc salicylate trihydrate

EXAMPLES 1 TO 7 AND COMPARATIVE EXAMPLES 1 TO 7

Ink compositions were prepared by blending the materials in the properties (%) shown below in Table 1

TABLE 1

| | A | B | C | D | E | F | G |
|---|---|---|---|---|---|---|---|
| Example | | | | | | | |
| 1 | A-1 0.3 | B-1 10.0 | C-1 1.0 | D-1 61.4 | E-1 0.1 | F-1 20.0 F-2 5.0 | G-1 2.2 |
| 2 | A-1 0.8 | B-2 6.0 | C-2 1.5 | D-2 91.7 | — | — | — |
| 3 | A-1 0.5 | B-3 5.0 | C-3 2.8 | D-3 76.7 | — | F-3 10.0 | G-2 5.0 |
| 4 | A-2 0.4 | B-4 8.0 | C-4 2.0 | D-4 89.6 | — | — | — |
| 5 | A-3 1.1 | B-5 25.0 | C-5 1.2 | D-1 35.0 D-5 15.0 | — | F-4 22.0 | G-3 0.7 |
| 6 | A-1 1.5 | B-6 18.0 | C-6 4.3 | D-4 51.0 D-5 21.2 | — | F-5 4.0 | — |
| 7 | A-2 2.5 | B-4 12.0 | C-6 3.7 | D-1 81.8 | — | — | — |
| Comparative Example | | | | | | | |
| 1 | A-1 0.3 | B-1 10.0 | — | D-1 61.4 62.4 | E-1 0.1 | F-1 20.0 F-2 5.0 | G-1 2.2 |
| 2 | A-1 0.8 | B-2 6.0 | — | D-2 93.2 | — | — | — |
| 3 | A-1 0.5 | B-3 5.0 | — | D-3 80.5 | — | F-3 9.0 | G-2 5.0 |
| 4 | A-2 0.4 | B-4 8.0 | — | D-4 91.6 | — | — | — |
| 5 | A-3 1.1 | B-5 25.0 | — | D-1 36.2 D-5 15.0 | — | F-4 22.0 | G-3 0.7 |
| 6 | A-1 1.5 | B-6 18.0 | — | D-4 55.3 D-5 21.2 | — | F-5 4.0 | — |
| 7 | A-2 2.5 | B-4 12.0 | — | D-1 85.5 | — | — | — |

Filter paper sheets were respectively immersed in the ink compositions obtained in the above manner and then dried to give test specimens. These specimens were placed in an airtight container and allowed to stand at a temperature of 50° C. in an atmosphere containing 500 mg/liter of ethylene oxide for 2 hours (a) in the presence of water vapor (50% relative humidity) or (b) in the absence of water vapor (0% relative humidity) and, then, measured for the color difference ΔE resulting from color change using a direct-reading digital color difference meter (model "ND-5044AA"; Nippon Denshoku Kogyo Kabushiki Kaisha). The results are shown in Table 2. The changes in color (color development) before and after placed in the state (a) as observed for the specimens are also shown in Table 2.

TABLE 2

| | (a) | (b) | (a) − (b) | Color development |
|---|---|---|---|---|
| Example | | | | |
| 1 | 38.8 | 16.2 | 22.6 | Brown - green |
| 2 | 26.2 | 5.2 | 21.0 | Purple - azure |
| 3 | 35.1 | 11.4 | 23.7 | Red - blue |
| 4 | 29.8 | 7.3 | 22.5 | Purple red - purple blue |
| 5 | 35.4 | 15.2 | 20.2 | Purple - blue |
| 6 | 32.1 | 10.2 | 21.9 | Purple - azure |
| 7 | 25.1 | 3.9 | 21.2 | Purple red - purple blue |
| Comparative example | | | | |
| 1 | 22.6 | 9.3 | 13.3 | Brown - green |
| 2 | 20.6 | 15.2 | 5.4 | Purple - azure |
| 3 | 18.4 | 9.5 | 8.9 | Red - blue |
| 4 | 25.4 | 17.9 | 7.5 | Purple red - purple blue |
| 5 | 27.8 | 21.2 | 6.6 | Purple - blue |
| 6 | 24.7 | 14.1 | 10.6 | Purple - azure |
| 7 | 20.1 | 11.8 | 8.3 | Purple red - purple blue |

The results shown in Table 2 clearly indicate that the ink compositions of the present invention in which an ultrafine filler is used have excellent properties as a sterilization indicator ink.

REFERENCE EXAMPLE 1

Using the in composition of Example 1 and the ink composition of Comparative Example 1, test specimens were prepared in the same manner as above and then they were treated in the same manner as described above except that the treatment time was varied. The changes in color of the test specimens were then observed.

The results thus obtained are shown in FIG. 1. The curves in FIG. 1 respectively correspond to the following conditions.

1—Ink of Comparative Example 1, relative humidity 0%.

2—Ink of Comparative Example 1, relative humidity 50%.

3—Ink of Example 1, relative humidity 0%.

4—Ink of Example 1, relative humidity 50%. The results shown in FIG. 1 also clearly indicate that the ink composition of the present invention in which an ultrafine filler is used shows excellent characteristics.

Figure 1:
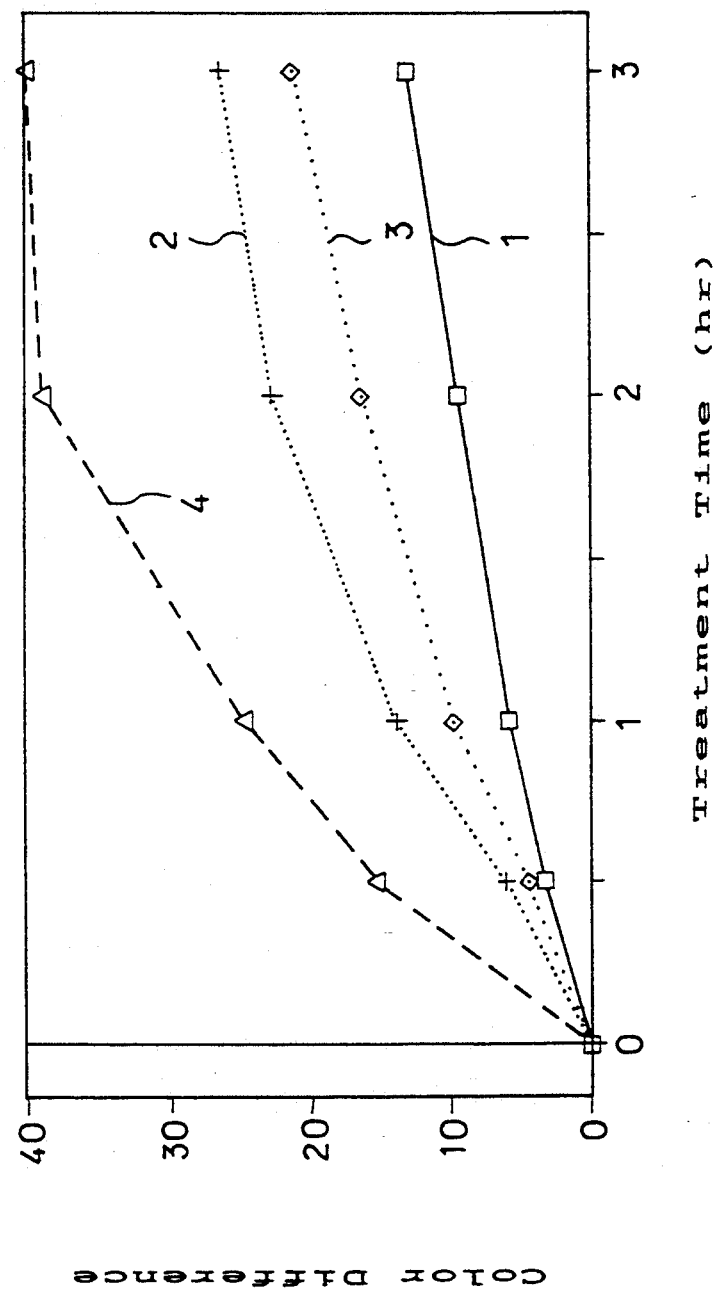
FIG. 1 graphically shows the color changing behaviors of the ink compositions obtained in Example 1 and Comparative Example 1 in the presence of ethylene oxide (EO).

I claim:

1. An ink composition for indicating the progress of sterilization with ethylene oxide which comprises;
   (1) at least one disperse dye of the general formula A—N=N—B 

wherein A is the residue of a heterocyclic compound containing a nitrogen atom which is not substituted with an alkyl group and selected from the group consisting of the pyridine, quinoline, isoquinoline, triazole, tetrazole, indazole, thiazole, benzothiazole and thiadiazole rings, which residue may optionally have one or more undissociated substituents, and B is a coupling component,
   (2) at least one binder component selected from the group consisting of polyacrylic acid, polymethacrylic acid and acrylic acid-methacrylic acid copolymers,
   (3) at least one ultrafine filler selected from the group consisting of ultrafine particles of aluminum oxide and titanium oxide and having a mean primary particle size of about 5 to about 100 nm and a specific surface area of about 10 to about 1,000 m²/g as determined by the BET method, and
   (4) at least one polar solvent, the amount of components (1), (2), (3) and (4) being 0.05 to 3%, 0.5 to 50%, 0.05 to 10% and 30 to 95%, respectively, based on the weight of the ink.

2. An ink composition as claimed in claim 1 wherein the polar solvent is selected from the group consisting of water, aliphatic alcohols and glycol ethers.

3. An ink composition as claimed in claim 1 wherein
   (1) the disperse dye is at least one species selected from the group consisting of C.I. Disperse Red 58, 88, 111 and 206, C.I. Disperse Violet 43 and C.I. Disperse Blue 102,
   (2) the binder component is at least one member of the group consisting of polyacrylic acid and acrylic acid-methacrylic acid copolymers,
   (3) the ultrafine filler is aluminum oxide ultrafine particles, and
   (4) the polar solvent is at least one species selected from the group consisting of water, aliphatic alcohols and glycol ethers.

4. An ink composition as claimed in claim 1 which further contains at least one resin selected from the group consisting of carboxyl- or phenolic hydroxyl group-containing resins and cellulosic resins.

5. An ink composition as claimed in claim 1 which further contains at least one organic acid in an amount of not more than 10%, based on the weight of the ink.

6. A method of indicating the progress of ethylene oxide sterilization which comprises using an ink composition comprising;
   (1) at least one disperse dye of the general formula A—N=N—B 

wherein A is the residue of a heterocyclic compound containing a nitrogen atom which is not substituted with an alkyl group and selected from the group consisting of the pyridine, quinoline, isoquinoline, triazole, tetrazole, indazole, thiazole, benzothiazole and thiadiazole rings, which residue may optionally have one or more undissociated substituents, and B is a coupling component,
   (2) at least one binder component selected from the group consisting of polyarcylic acid, polymethacrylic acid and acrylic acid-methacrylic acid copolymers,
   (3) at least one ultrafine filler selected from the group consisting of ultrafine particles of aluminum oxide and titanium oxide and having a mean primary particle size of about 5 to about 100 nm and a specific surface area of about 10 to about 1,000 m²/g as determined by the BET method, and
   (4) at least one polar solvent, the amount of components (1), (2), (3) and (4) being 0.05 to 3%, 0.5 to 50%, 0.05 to 10% and 30 to 95%, respectively, based on the weight of the ink.

7. A method as claimed in claim 6 wherein the polar solvent is selected from the group consisting of water, aliphatic alcohols and glycol ethers.

8. A method as claimed in claim 6 wherein
   (1) the disperse dye is at least one species selected from the group consisting of C.I. Disperse Red 58, 88, 111 and 206, C.I. Disperse Violet 43 and C.I. Disperse Blue 102,
   (2) the binder component is at least one member of the group consisting of polyacrylic acid and acrylic acid-methacrylic acid copolymers, (3) the ultrafine filler is aluminum oxide ultrafine particles, and (4) the polar solvent is at least one species selected from the group consisting of water, aliphatic alcohols and glycol ethers.

9. A method as claimed in claim 6 wherein the ink composition further contains at least one resin selected from the group consisting of carboxyl- or phenolic hydroxyl group-containing resins and cellulosic resins.

10. A method as claimed in claim 6 wherein the ink composition further contains at least one organic acid in an amount of not more than 10% based on the weight of the ink.

* * * * *